United States Patent [19]
von Berg

[11] Patent Number: 5,540,100
[45] Date of Patent: Jul. 30, 1996

[54] PRESSURE TRANSDUCER FOR MEASURING THE PRESSURE OF A FLUID, IN PARTICULAR FOR INVASIVE BLOOD PRESSURE MEASUREMENTS

[75] Inventor: Peter von Berg, Tiburon, Calif.

[73] Assignee: PVB Medizintechnik GmbH, Germany

[21] Appl. No.: 372,439

[22] Filed: Jan. 12, 1995

[30] Foreign Application Priority Data

Jan. 14, 1994 [DE] Germany .................. 44 00 941.0

[51] Int. Cl.[6] .................. G01L 7/00; A61B 5/02
[52] U.S. Cl. .................. 73/756; 73/715; 73/714; 128/675
[58] Field of Search .................. 73/706, 715, 723, 73/727, 748, 756, 708, 714; 128/675, 672, 673

[56] References Cited

U.S. PATENT DOCUMENTS

| | | | |
|---|---|---|---|
| 4,023,562 | 5/1977 | Hynecek et al. | 128/2.05 E |
| 4,329,878 | 5/1982 | Utner et al. | 73/766 |
| 4,340,877 | 7/1982 | Herden | 338/42 |
| 4,576,181 | 3/1986 | Wallace et al. | 128/675 |
| 4,603,574 | 8/1986 | Norman | 73/4 R |
| 4,679,657 | 7/1987 | Hanlon et al. | 128/675 |
| 4,732,044 | 5/1988 | Dell'Acqua et al. | 73/727 |
| 4,825,876 | 5/1989 | Beard | 128/675 |
| 4,838,089 | 6/1989 | Okada et al. | 73/727 |
| 4,970,900 | 11/1990 | Sherpherd et al. | 73/756 |
| 5,014,557 | 5/1991 | Lawless | 73/756 |
| 5,097,841 | 3/1992 | Moriuchi et al. | 128/675 |
| 5,237,994 | 8/1993 | Goldberg | 128/633 |
| 5,351,550 | 10/1994 | Maurer | 73/727 |

FOREIGN PATENT DOCUMENTS

| | | |
|---|---|---|
| 0124308B1 | 1/1988 | European Pat. Off. . |
| 0360286A2 | 3/1990 | European Pat. Off. . |
| 0129779B1 | 4/1991 | European Pat. Off. . |
| 0366651B1 | 11/1992 | European Pat. Off. . |
| 2125991 | 9/1972 | France . |
| 2916390A1 | 4/1979 | Germany .................. G01D 5/16 |
| 2946515A1 | 11/1979 | Germany .................. G01L 9/14 |
| 3207044A1 | 2/1982 | Germany .................. A61B 5/02 |
| 8601071 U | 1/1986 | Germany .................. G01L 9/04 |
| 3631659A1 | 9/1986 | Germany .................. G01L 9/04 |
| 8908951 U | 7/1989 | Germany .................. G01L 9/04 |

OTHER PUBLICATIONS

Health Devices, Mar. 1988, pp. 75–94.
Health Devices, Sep. 1984, pp. 268–290.
Cobe Disposable Transducer, 1983.

*Primary Examiner*—Richard Chilcot
*Assistant Examiner*—Paul D. Amvozowicz
*Attorney, Agent, or Firm*—Senniger, Powers, Leavitt & Roedel

[57] ABSTRACT

A pressure transducer for measuring the pressure of a fluid, in particular for invasive blood pressure measurements, comprises a housing with two chambers that are separated from one another in a fluid-proof fashion, whereby the first chamber accommodates a pressure transducer that is fastened onto a substrate and may be charged with the pressure of the fluid to be measured. The substrate lies in both chambers and has contact surfaces for the direct connection of an electric plug-in connector within the region of the second chamber. This plug-in connector comprises parallel tongues between which the substrate and a housing cover may be accommodated. One of the tongues carries electric spring contacts.

11 Claims, 7 Drawing Sheets

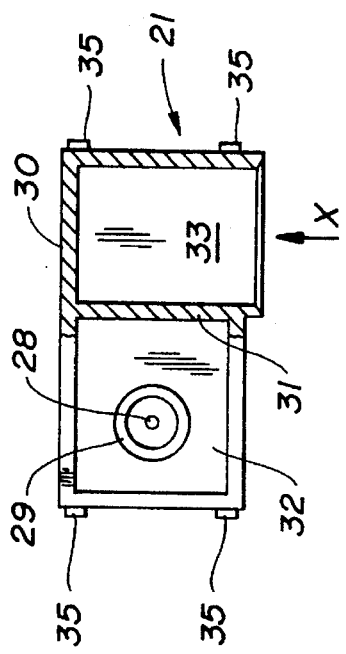
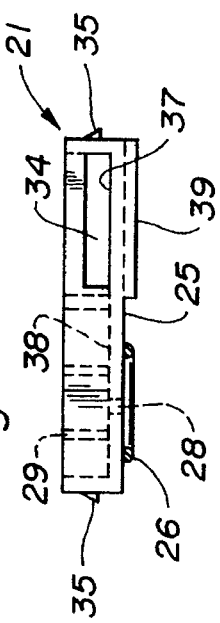
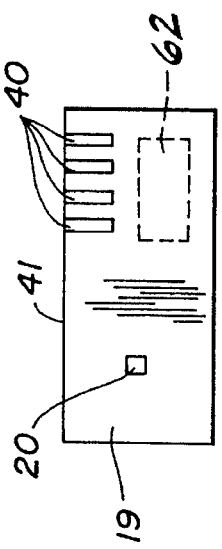
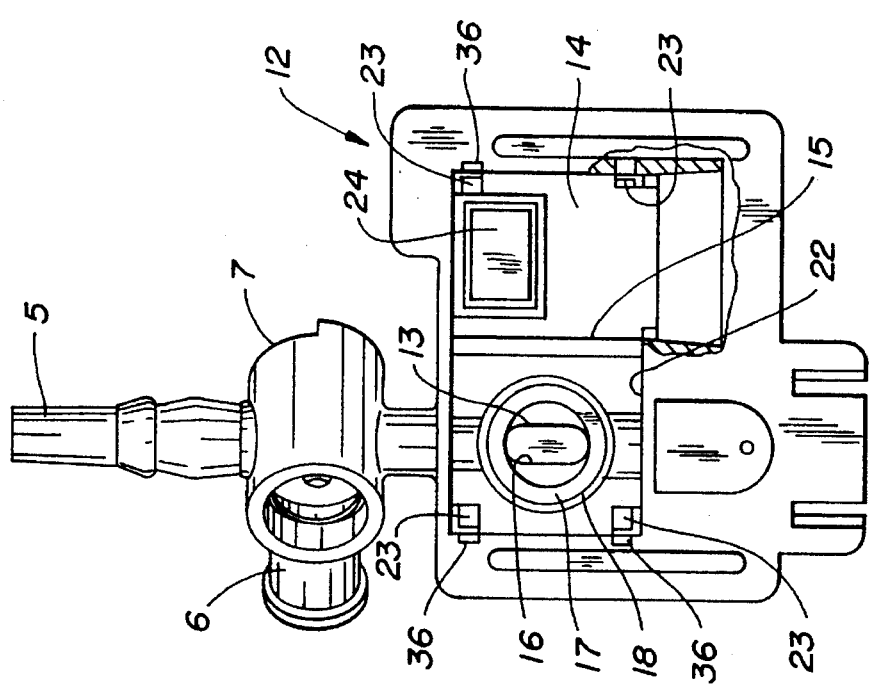

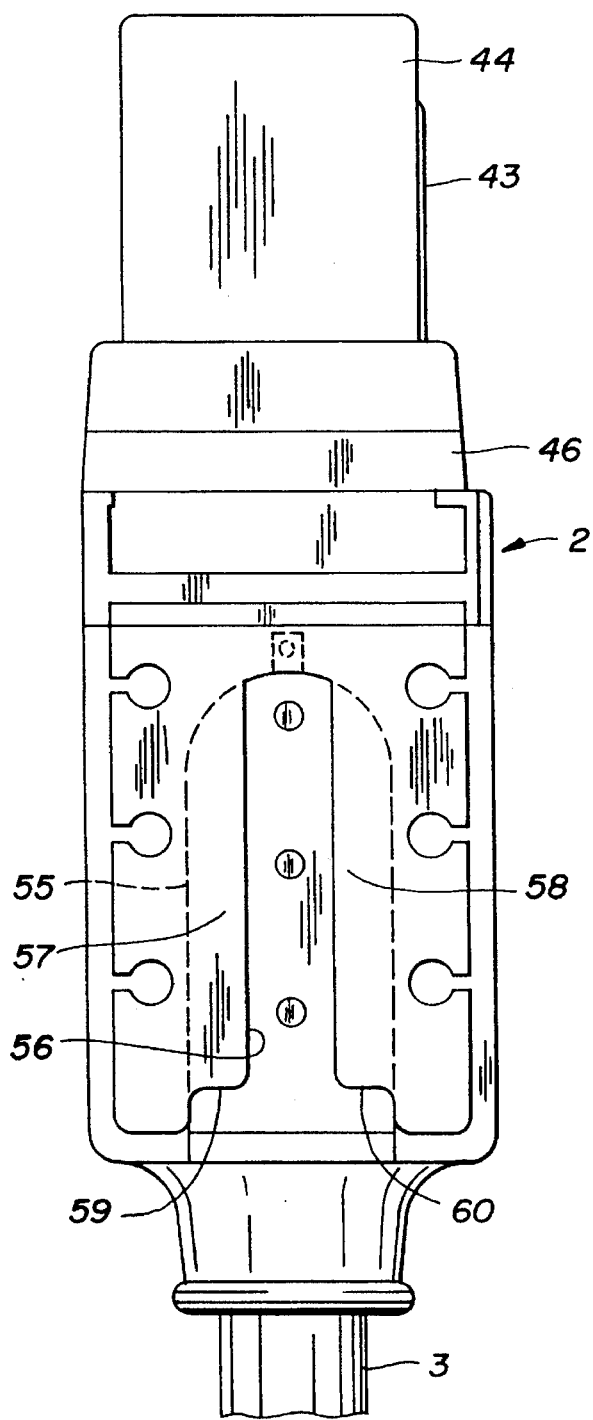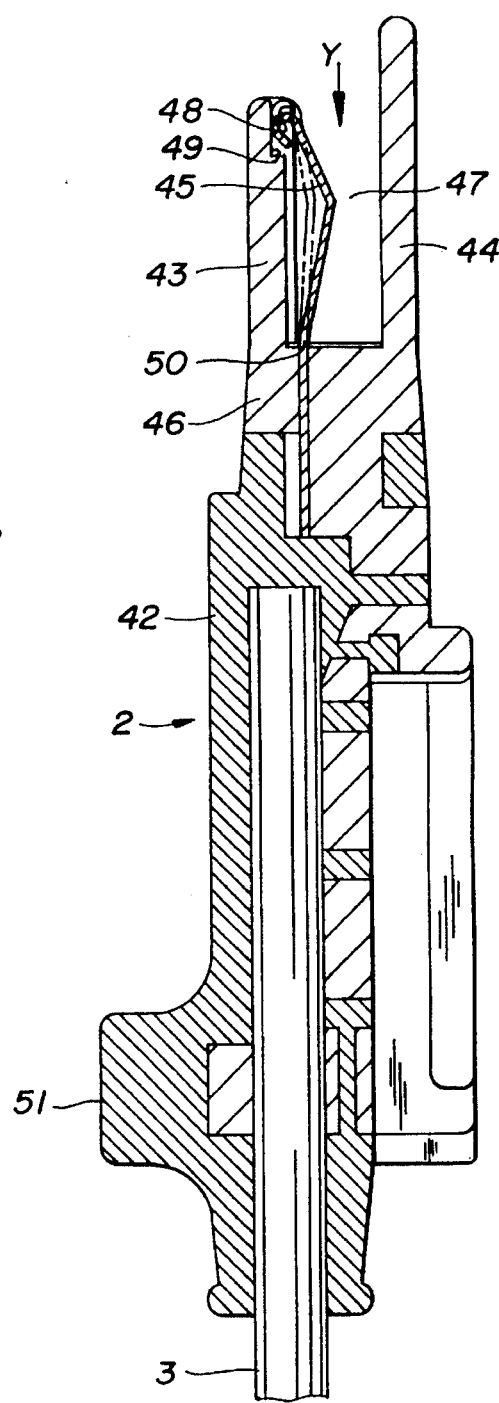

PRESSURE TRANSDUCER FOR MEASURING THE PRESSURE OF A FLUID, IN PARTICULAR FOR INVASIVE BLOOD PRESSURE MEASUREMENTS

BACKGROUND OF THE INVENTION

The invention pertains to a pressure transducer and, in particular, to a pressure transducer for invasive blood pressure measurements.

A pressure transducer of this type is known from European Patent No. 0,360,286A2. In this case, a pressure measuring element is fastened onto a flat substrate. Electric conductors arranged on the substrate extend laterally to contact points arranged on the edge of the substrate. An electric cable is soldered onto these contact points.

French Patent No. 2,125,991 describes a similar pressure transducer with a housing that is divided into two separate chambers in a fluid-proof fashion via a membrane, whereby the first chamber is connected to an inlet opening and an outlet opening for the fluid. The second chamber contains a pressure measuring element that converts the fluid pressure that is applied to the said pressure measuring element via the membrane into electronic signals. These signals are transmitted from the second chamber toward the outside via electric conductors.

These devices are reusable pressure transducers with a so-called pressure dome that may be unscrewed, cleaned and sterilized after being used such that they may be reused. Due to the high expenditures associated with the cleaning and sterilization process, disposable pressure transducers primarily have been used for medical purposes since the beginning of the 1990's. These disposable pressure transducers are easier to handle with respect to their operation, maintenance, etc., and significantly reduce the risk of infection for the patient. In these instances, miniaturized pressure measuring elements are used that are fastened onto a ceramic substrate which, in the form of a printed circuit, also contains the external wiring of the pressure measuring element or balancing resistors, etc., and printed conductors. A pressure measuring element of this type is disclosed in U.S. Pat. No. 4,023,562.

Pressure measuring elements of this type in principle are designed in the form of a Wheatstone bridge circuit with a resistive wire strain gauge or another transducer that converts a pressure or a mechanical load into electronic signals, e.g., transducers known from German Patent (OLS) No. 2,916,390.

The first pressure transducer that is used for blood pressure measurements and operates with such pressure measuring elements is described in the company prospectus "Disposable Transducers" that was published by the firm Cobe Laboratories Inc. in 1983. In this pressure transducer, the ceramic substrate with the pressure measuring element was inserted into a pressure measuring chamber that was closed in a fluid-proof fashion and connected to an inlet opening and an outlet opening for the fluid. The electric connections for ascertaining the measured values extended laterally from this chamber in the form of printed conductors and were rigidly soldered at this location onto a cable connected to the housing of the pressure transducer.

German Patent No. 2,946,515 A1 discloses a pressure transducer with Hall IC in which the electric conductors of the pressure measuring element extend to plug-in contacts that are rigidly arranged in the housing. These plug-in contacts produce the electric connection with a cable via a plug/socket connection.

One additional pressure transducer for invasive blood pressure measurements is disclosed in German Patent No. 3,207,044 A1.

This transducer also is designed as a disposable device that comprises an integrated stop valve for drawing blood to be analyzed. In addition, this pressure transducer comprises an integrated capillary system for carrying out a rapid rinsing process.

Different types of disposable pressure transducers are described in the journal *Health Devices* of September, 1983, pp. 268–290, in an article entitled "Disposable Pressure Transducers." In some of these pressure transducers, certain electronic components and balancing resistors are accommodated in the reusable cable.

European Patent No. 0,124,308-B1 discloses a similar pressure transducer in which the pressure measuring element is inserted into an electrically insulated body in the form of a capsule and arranged such that it faces the chamber that contains the fluid to be measured. In this case, the electric conductor extends through the electrically insulated body and ends in connecting means inside of the housing so as to produce a connection for electronic circuitry.

European Patent No. 0,129,779 B1 discloses a similar pressure transducer with a plug/socket connection for connecting a reusable electric cable as well as a balancing card that is arranged in the cable and serves for balancing the resistors of the pressure transducer.

U.S. Pat. No. 4,603,574 discloses a pressure transducer in which a test resistor is arranged parallel to one branch of the Wheatstone bridge circuit in order to test the pressure transducer. The test resistor is connected in parallel to this branch in order to obtain a defined display value by simultaneously actuating two electronic switches. These two switches may be accommodated on the pressure transducer itself or in the supply cable.

German Patent No. 3,631,659 A1 discloses a pressure transducer for general purposes with a pin/socket connection for connecting the electric cable. The same also applies to German Utility Model No. 8,601,071.

European Patent No. 0,366,651 B1 discloses a pressure transducer with a short, rigidly soldered cable that is discarded together with the pressure transducer after use. This cable has a plug-in connection in order to be connected to an additional cable, whereby said additional cable is reusable and contains an electronic switch and a shunt resistor that is switched in parallel to one branch of the bridge circuit when depressing the switch so as to generate a defined display value.

The journal *Health Devices* of March, 1988, Vol. 17, No. 3, pp. 75–94 discloses additional disposable pressure transducers with one common characteristic, namely that a short cable that may be connected to a cable leading to the monitor via a plug-in connection is rigidly arranged on the pressure transducer.

German Utility Model No. 8,908,951 discloses a pressure sensor with an integrated plug housing.

The invention is based on the objective of improving the pressure transducer of the initially mentioned type in such a way that it has a simple and compact design, may be mounted in simple and inexpensive fashion, comprises only a few disposable parts, provides for simple and safe handling and, in particular, comprises a simple and safe electric connection to the cable leading to the monitor or another display device.

According to the invention, this objective is attained by the characteristics disclosed in claim 1. Advantageous embodiments and developments of the invention are disclosed in the subclaims.

Briefly stated, the disposable part of the pressure transducer according to the invention comprises only one housing and one substrate that is equipped with electric circuits and a pressure measuring element. The electric cable is connected by means of a special plug-in connector which directly contacts the contact surfaces of the substrate, i.e., without additional intermediate cable sections, overlapping the substrate and one housing cover in the fashion of pliers, and consequently produces the contact while largely relieving the substrate of mechanical loading.

The substrate according to one embodiment of the invention is simply placed into the housing and is retained therein by means of a preferably detachable cover.

According to an additional embodiment of the invention, the cover has an opening for one tongue of the plug-in connector. Consequently, the plug-in connector encompasses the substrate and the cover in the fashion of pliers. Since the entire surface of the cover adjoins the substrate, all mechanical forces generated by the plug-in connector also are absorbed by it.

The first chamber that contains the pressure measuring element is limited by one section of the substrate and insulated in a fluid-proof fashion via an annular seal that presses against the substrate. One additional annular seal is arranged on the cover such that it is situated essentially congruent to the aforementioned annular seal, whereby said additional annular seal presses against the side of the substrate situated opposite to the first chamber and consequently seals an opening that extends through the substrate and serves for balancing or calibrating the pressure transducer.

The fluid connections and a rinsing system are integrated into the housing of the pressure transducer such that they form a single component. In addition, a test key is integrated into the housing, whereby said test key is retained and guided in an opening of the housing, comprising at least one switching contact surface on its side that faces the substrate and cooperating with the switching contact surfaces that are printed on the substrate so as to test the system. This key consists of an elastic material, whereby the switching contact surfaces are arranged in such a way that no contact with the switching contact surfaces arranged on the substrate is produced if the key is not actuated due to the resilience of the elastic material. Consequently, no separate spring for the key is required as is the case with pressure transducers of the state of the art.

According to an additional embodiment of the invention, the pressure transducer and the plug-in connector may be fixed onto a holding plate that aligns the two aforementioned components in the correct position to one another and allows their coupling.

BRIEF DESCRIPTION OF THE DRAWINGS

The invention is described in detail below with reference to one embodiment that is illustrated in the figures. The figures show:

FIG. 4: view of the lower side of the pressure transducer, whereby the housing is opened and the substrate is removed;

FIG. 5: a view of the outer side of a cover that closes the housing of the pressure transducer;

FIG. 6: a view of the cover according to FIG. 5, viewed in the direction of the arrow X of FIG. 5;

FIG. 7: a top view of the substrate used in the pressure transducer with the pressure measuring element arranged thereon;

FIG. 8: a lateral cross section of a plug that may be connected to the pressure transducer;

FIG. 9: a view of the lower side of the plug according to FIG. 8;

DETAILED DESCRIPTION OF THE INVENTION

Figure 1:
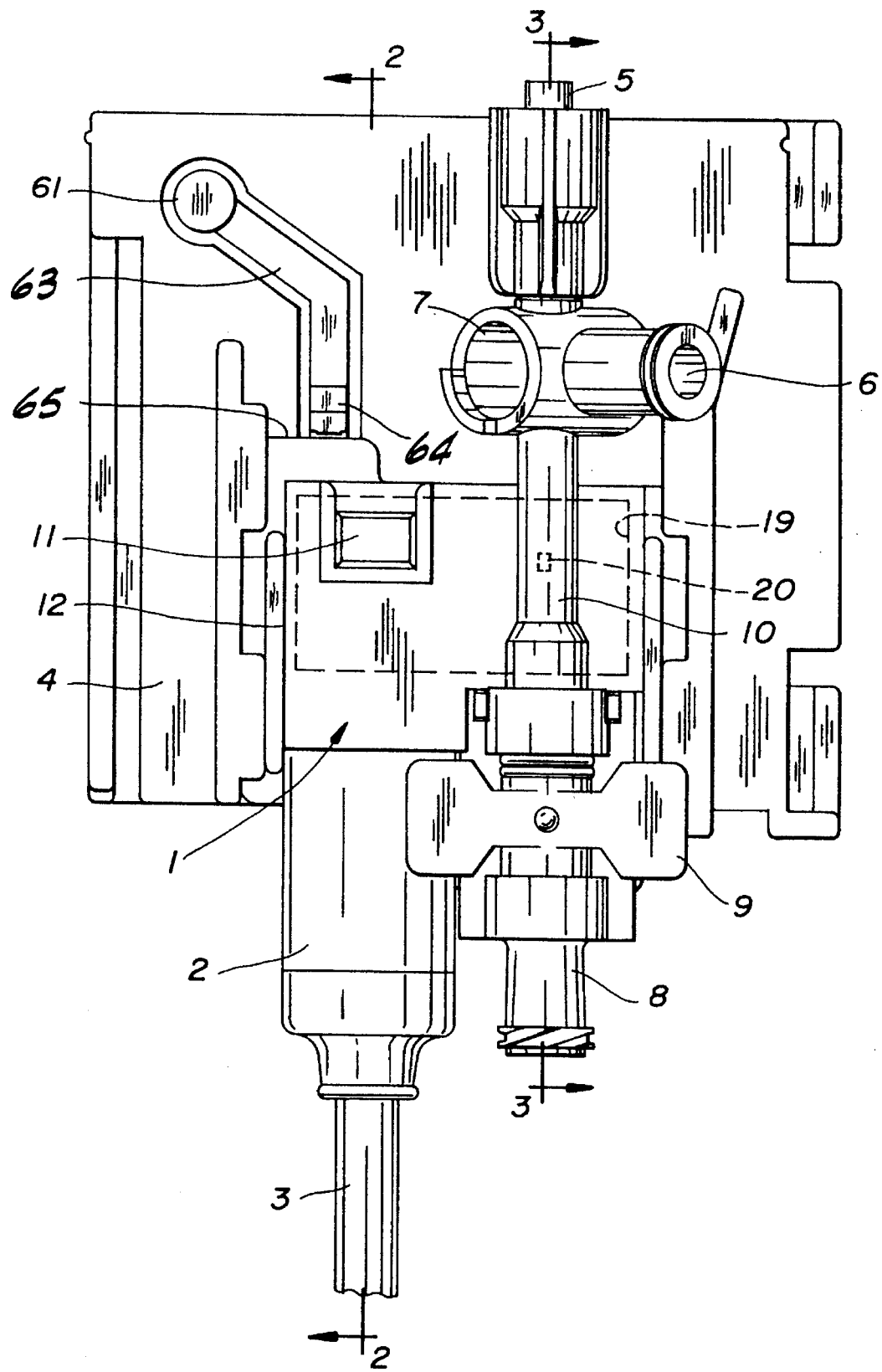
FIG. 1: a top view of a pressure transducer according to the invention that is fixed onto a holding plate.

The pressure transducer which is identified as a whole by the reference numeral 1 is electrically connected to a cable 3 via a plug-in connector 2, whereby said cable usually is connected to a monitor. While being inserted, the unit comprising the pressure transducer 1 and the plug-in connector 2 is fastened onto a holding plate 4, whereby the pressure transducer 1 and the plug-in connector 2 each may be fixed separately onto the holding plate 4—as will be described in detail below with reference to FIGS. 9–12—such that the coupling process also may be carried out in cooperation with the holding plate. The pressure transducer has a first connection 5 for a fluid that normally is connected to a blood vessel of the patient via a tube. A second connection 6 for a fluid serves for supplying an additional fluid, e.g., a salt solution, that is used for initially filling the system as well as preventing a possible blockage of the system due to coagulated blood. A three-way valve is provided between the two connections 5 and 6, whereby an opening 7 for a valve plug 7' (FIG. 3) can be seen in FIG. 1. In addition, the pressure transducer comprises an opening 8 that is connected to the end of a pressure measuring line 10 that is situated opposite to the openings 5 and 6 via a rinsing valve 9. The valve 9 and the opening 8 serve for rinsing the system and, in particular, discharging air bubbles during the initial filling process. The pressure measuring line 10 is an integrated component of the pressure transducer 1 and conveys the liquid, the pressure of which should be measured, to an additional pressure measuring chamber that is described in detail below.

The pressure transducer 1 comprises a test key 11 that is guided in the housing 12 of the pressure transducer and actuates an electronic switch that allows a functional test of the pressure transducer. According to the state of the art, this switch alters one branch of a measuring bridge in a defined fashion, e.g., by connection of a test resistor in parallel via one branch of the bridge, whereafter a defined value of, for example, 100 mm Hg is displayed on the monitor if the pressure transducer operates properly and all electric connections are produced correctly.

Two chambers 13 and 14 (FIG. 4) that are separated from one another in a fluid-proof fashion are arranged in the interior of the pressure transducer. The first chamber 13 is the "measuring chamber" that is connected to the pressure measuring line 10 for the fluid, while the second chamber 14 is used for producing the electronic connections between the plug-in connector 2 and a pressure measuring element. These two chambers are separated from one another by means of a crosspiece 15 (FIG. 4), whereby it should be noted that this crosspiece in the embodiment shown does not fulfill any sealing function for separating the two chambers 13 and 14 in a fluid-proof fashion.

The pressure measuring chamber 13 is connected to the pressure measuring line 10 via an opening 16, whereby an annular seal 17 in the form of a silicone O-ring is arranged around this opening while being held in position by a cylindrical guide 18.

A substrate 19 is situated in the interior of the pressure transducer. In this case, the substrate is a ceramic plate (compare to FIG. 7) and carries a pressure measuring element 20 that is situated within the region of the chamber 113. This substrate is inserted into the interior of the pressure transducer 1 and is supported on the annular seal 17, so that the annular seal 17 and the region of the substrate enclosed by said annular seal ensure that the measuring chamber 13 is sealed in fluid-proof fashion. A housing cover 21 is provided on the side of the substrate which is situated opposite the measuring chamber 13. This housing cover may be inserted into an essentially rectangular housing opening 22 and fixed at this location in detachable fashion. Four supports 23 (FIG. 4) are arranged within the region of this opening, whereby the substrate that is held in position by the cover 21 on the opposite side is supported itself on the aforementioned supports.

According to FIG. 4, a rectangular opening 24 for accommodating and guiding the test key 11 is provided within the region of the second chamber 14.

The base 25 (FIG. 6) of the cover 21 which faces the substrate 19 is entirely flat, so that the substrate may be supported against said cover over its entire surface. An annular groove is arranged in the base 25 of the cover 21, whereby said annular groove accommodates a second annular seal 26 that is arranged essentially congruent to the annular seal 17, so that the region of the substrate that is assigned to the chamber 13 is sealed via the annular seals 17 and 26. A small hole 27 that is aligned with a corresponding hole 28 in the housing cover 21 is situated at the location of the substrate on which the pressure measuring element 20 is arranged. The housing cover 21 has a cylindrical connection 29 around the opening 28, whereby a tube may be connected to said connection so as to apply a test pressure onto the side of the pressure measuring element 20 that is situated opposite to the measuring chamber 13. This makes it possible to carry out an accurate calibration with a defined reference pressure and simultaneously to apply atmospheric pressure as the reference pressure to the rear side of the pressure measuring element during normal operation.

FIG. 4 shows that the substrate 19 is inserted into the housing opening 22 and is supported on the supports 23 and the annular seal 17 and, if need be, also on the crosspiece 15. Subsequently, the cover 21 is inserted, whereby said cover adjoins the rear side of the substrate with its annular seal 26 and its flat base 25, and consequently holds the substrate in position. In this case, the pressure measuring element 20 of the substrate 19 lies in the measuring chamber such that it faces the measuring chamber 13.

The cover 21 (compare with FIGS. 5 and 6) has—as mentioned previously—a flat base 25, whereby vertical walls that form a frame 30, as well as a crosspiece 31 which, when assembled, lies parallel to the crosspiece 15, project from the aforementioned flat base. The frame 30 forms two rectangular regions 32 and 33, one on each side of this crosspiece 31, whereby said rectangular regions are situated opposite to the first or second chamber 13 or 14 of the pressure transducer. The two regions 32 and 33 have somewhat different dimensions in order to ensure that the cover may only be inserted in a defined position. The opening 22 is correspondingly adapted to this shape.

Catch projections 35 that engage into catch recesses 36 in the housing 12 and consequently lock the cover relative to the housing are arranged on two opposite walls of the frame 30. However, the cover may be easily removed by means of a tool, so that the plastic housing and the substrate with the metallic printed conductors and the pressure measuring element may be easily separated from one another when disposing of a used pressure transducer. This aspect is of particular importance with respect to strict environmental regulations.

The cover 21 is provided with a rectangular opening 34 on one face of the frame 30, whereby one edge 37 of said opening is aligned with the side 38 of the cover that is situated opposite to the base 25. This opening 34 serves for accommodating one tongue of the plug-in connector 2, as will be described in detail below with reference to FIG. 2. This opening 34 is arranged within the region 33 of the cover and consequently is aligned with the second chamber 14. The corresponding side wall 39 protrudes beyond the base 25 of the cover 21 within the region of this opening 34, so that this particular wall section forms a widened limit stop for inserting the plug-in connector 2.

FIG. 7 shows that the upper side of the substrate which is illustrated in FIG. 7 and faces the measuring chamber 13 in the assembled condition carries the pressure measuring element 20 and several contact surfaces 40 that extend laterally to one edge 41 of the substrate 19. These contact surfaces 40 are connected to the printed conductors (not shown in the figures) and to the pressure measuring element 20 and other externally arranged electronic conductors for the pressure measuring element 20 (not shown in the figures). In addition, FIG. 7 shows a region that is identified by a box 62 drawn in broken lines, wherein said region is situated opposite the test key 11 (FIG. 1) and comprises switching contact surfaces (not shown in the figures) which are electrically connected to one another by actuating the test key 11 in order to carry out the test function. The contact surfaces 40 are arranged within the region of the substrate 19 that lies in the second chamber 14 in the assembled condition of the pressure transducer, whereby the contact surfaces 40 lie on the side situated opposite the cover 21, i.e., on the side facing the interior of the housing.

FIG. 8 shows a more detailed embodiment of a plug-in connector 2 that comprises a plug housing 42 and two tongues 43 and 44 that extend parallel at a distance from one another and are arranged on the side 2 that is situated in front as viewed from the insertion direction. Electric spring contacts 45 that contact the contact surfaces 40 of the substrate if the plug-in connector is inserted are arranged between these two tongues. The spring contacts 45 are rigidly connected in a housing section 46 and extend into the intermediate space 47 between the two tongues 43 and 44. In this case, the free end 48 of the spring contacts 45 is bent in the shape of a hook and is supported on a recess 49 of the tongue 43 that points toward the intermediate space 47. The spring contacts are bent such that they point away from the tongue 43 and extend into the intermediate space 47 between the location 50 at which the spring contacts 45 are rigidly fastened and their free end 48, so that said spring contacts are able to generate the spring force required for pressing the spring contacts against the contact surfaces 40 of the substrate 19.

Figure 3:
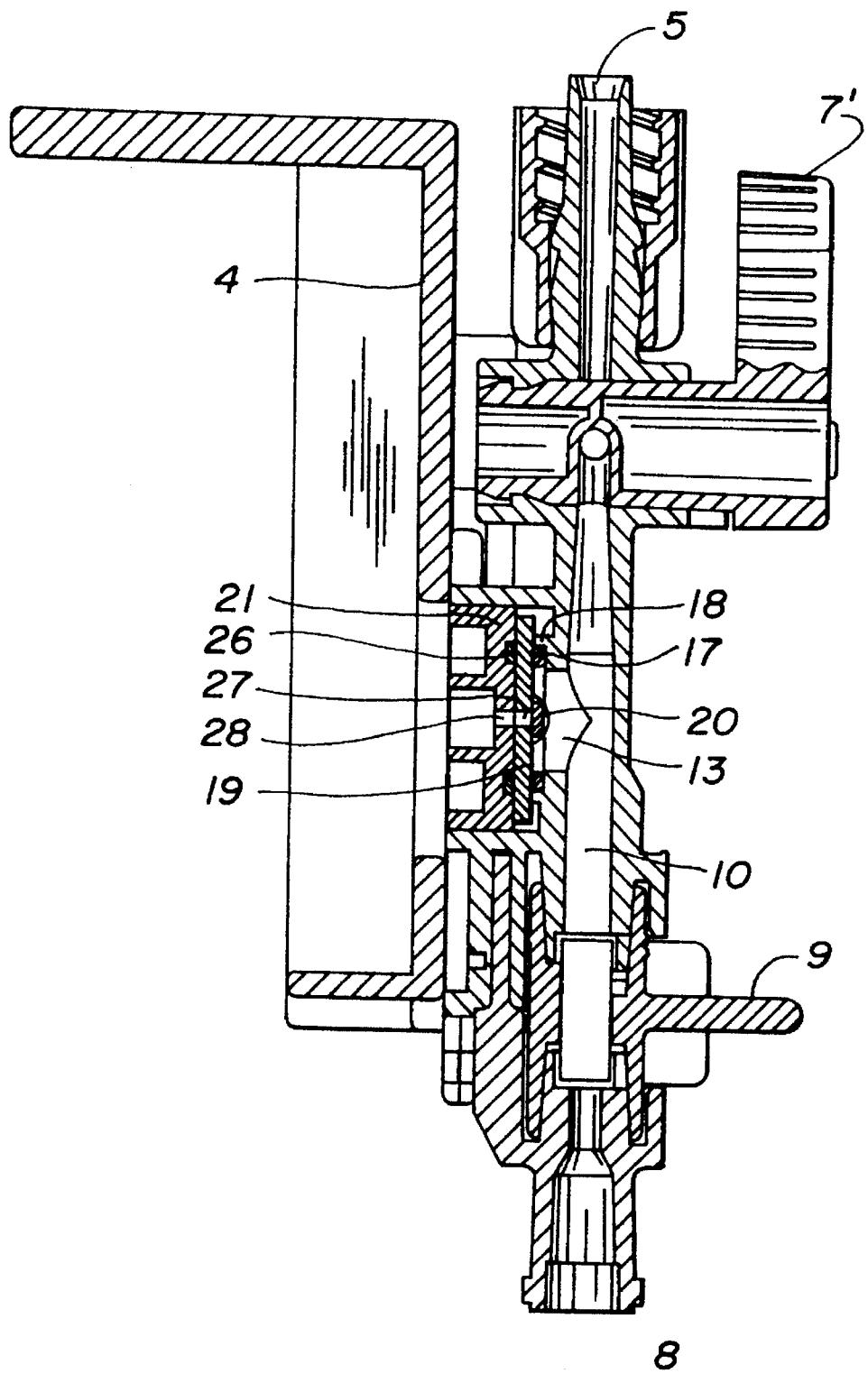
FIG. 3: cross section along the line II—II of FIG. 1.

The spring contacts 45 are connected to the assigned leads of the cable by means not illustrated in the figures, e.g., by soldering or cable clamps, wherein the cable 3 extends into the interior of the plug housing 42 and is held at this position, e.g., due to the fact that the plug housing 42 is extruded around the cable 3. The plug housing 42 consists of an elastic plastic material that is indicated in FIGS. 3 and 8 by double hatching. In contrast, the housing section 46 with the two tongues 43 and 44 consists of a harder material that also extends over additional parts of the plug housing 42 on the lower side (FIG. 9) and—as will be explained in detail below with reference to FIG. II—serves for holding the plug-in connector on the holding plate 4 (FIG. 1).

Figure 2:
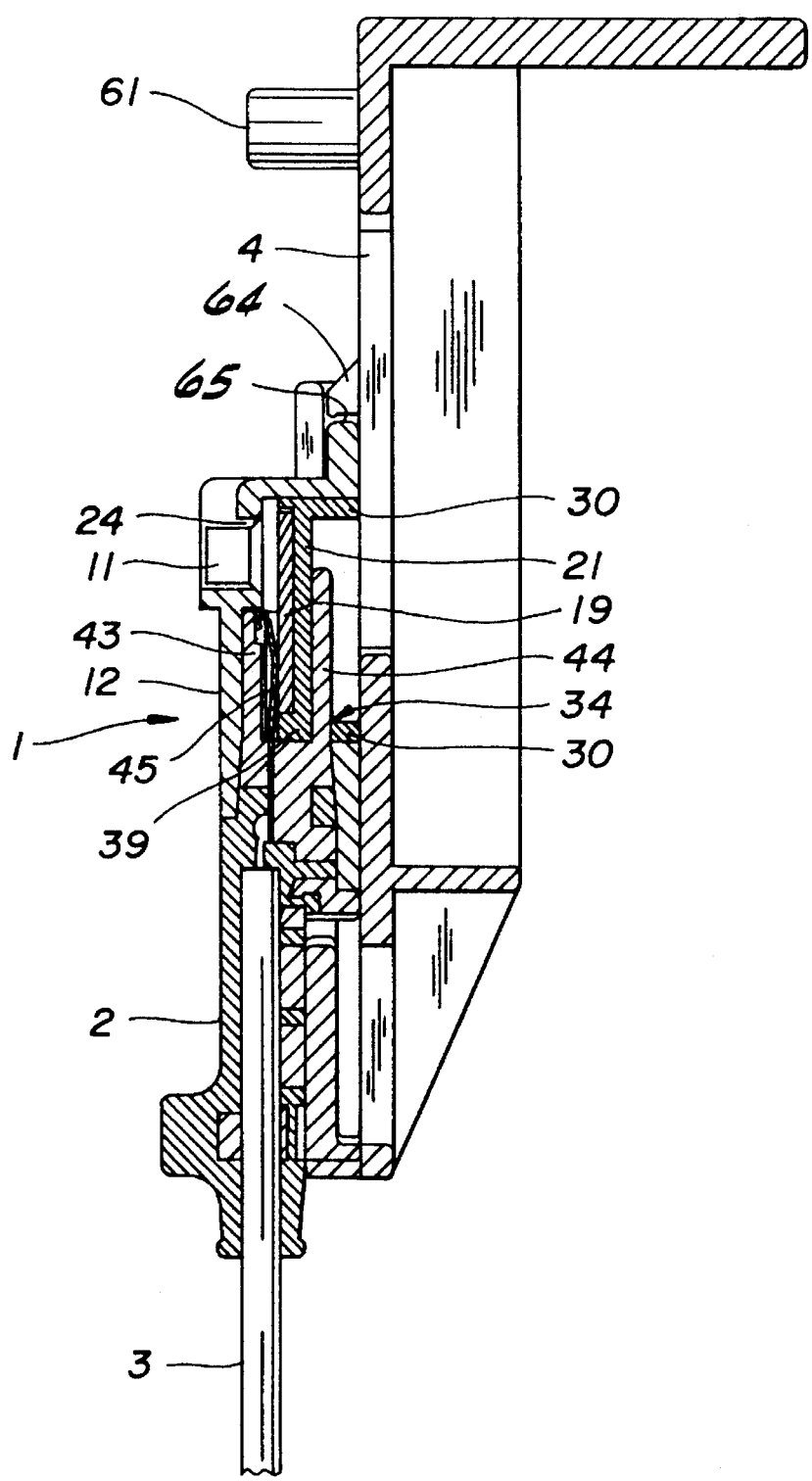
FIG. 2: cross section along line I—I of FIG. 1.
Figure 13:
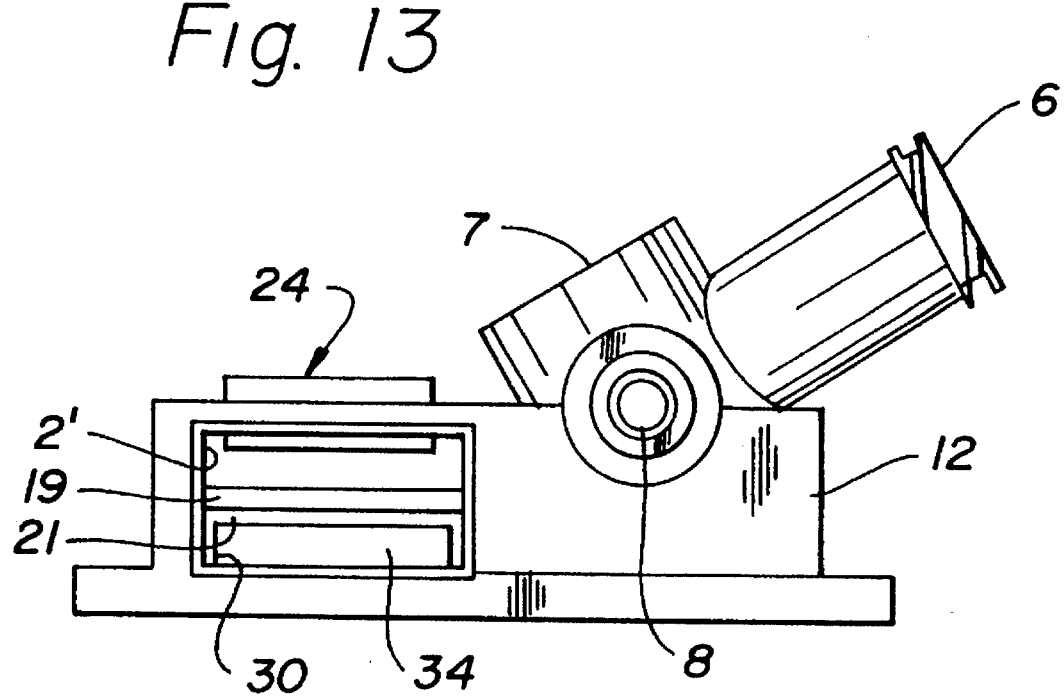
FIG. 13: a front view of the pressure transducer without the plug-in connector.

FIGS. 2 and 13 show that the housing 12 of the pressure transducer 1 is provided with a rectangular opening 2' into which the two tongues 43 and 44 as well as an adjacent part of the housing section 46 may be inserted. In this case, the two tongues 43 and 44 encompass the corresponding section of the substrate 19 and the housing cover 21, whereby the tongue 44 is inserted through the rectangular opening 34 of the housing cover. The tongue 43 with the spring contacts 45 consequently penetrates the second chamber 14 of the pressure transducer while the tongue 44 is situated outside of the housing of the pressure transducer. Due to the fact that both tongues 43 and 44 encompass the substrate 19 and the housing cover 21 in the fashion of pliers, both of these parts are supported on the two tongues 43 and 44 and the forces applied to the substrate by the spring contacts 45 are not only absorbed by the catch projections 35 of the housing part, but also by the tongue 44. Consequently, one obtains a retention of the (ceramic) substrate 19 in the housing of the pressure transducer that is largely free of mechanical loading.

Since the spring contacts 45 directly contact the contact surfaces 40 on the substrate, any additional circuitry required in previous pressure transducers are eliminated in the disposable pressure transducer according to the invention. This simplifies the manufacturing process and reduces the manufacturing expenditures such that the costs of the disposable pressure transducer are reduced for the given user. In addition, this simplifies subsequent disposal since no metallic parts that have to be separated from the plastic are present, except for the electric conductors that are printed onto the substrate and—as mentioned previously—may be easily separated from the plastic material of the housing by opening the cover 21 and removing the substrate.

The coupling and decoupling between the plug-in connector and the pressure transducer may be carried out manually in very simple fashion. In order to provide better handling for the separation of the connection, the plug housing is provided with a projection 51 for applying the required tensile forces, whereby pulling on the cable 3 by the user is prevented.

According to one additional embodiment of the invention, the plug-in connector 2 and the generally known holding plate 4 are modified in such a way that the coupling and holding of the plug-in connector is simplified and the components to be coupled to one another, i.e., the pressure transducer 1 and the plug-in connector 2, are correctly guided or held in their respectively aligned position during the coupling and decoupling process. When using the pressure transducer, the pressure transducer and the plug-in connector are held in their mutually coupled position by the holding plate, so that an unintentional separation of the plug-in connector, e.g., by tension on the cable, is prevented.

The holding plate 4 which is generally known from the not previously published Patent Application No. P 43 17 985.1 comprises a projection 52 that for this purpose protrudes beyond the otherwise rectangular contour, whereby the plug-in connector 2 is positioned and held via said projection in its correctly aligned position relative to the pressure transducer 1. The projection 52 lies in the plane of the holding plate 4 and is provided with an interlocking projection 53 that protrudes from this plane and has a T-shaped cross section (compare to FIG. 12). At the end situated opposite to the holding plate 4, the interlocking projection 53 is limited by a wall that extends perpendicular to its longitudinal direction and serves as a limit stop 54.

Figure 11:
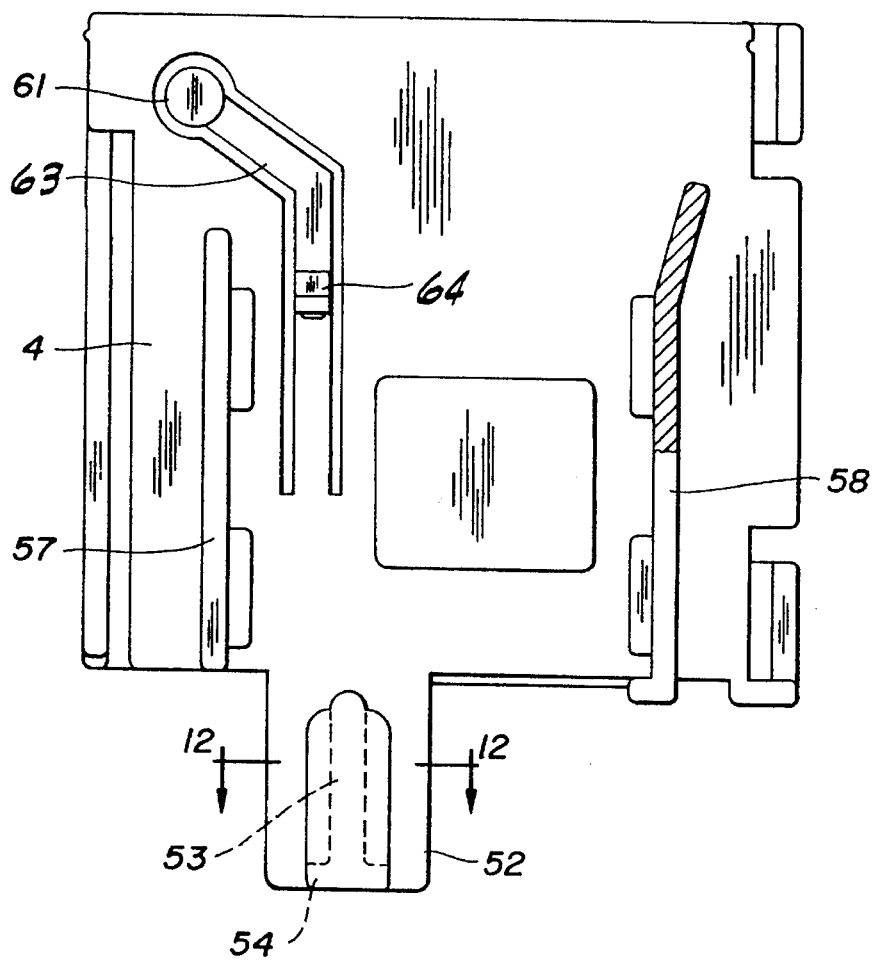
FIG. 11: a top view of a holding plate for fixing the pressure transducer and the plug.
Figure 12:
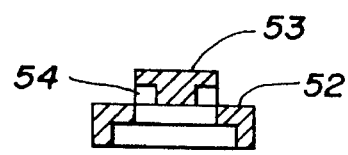
FIG. 12: a cross section along line III—III of FIG. 11.
Figure 10:
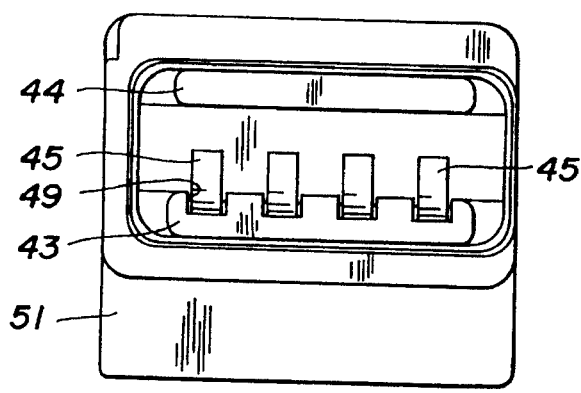
FIG. 10: a view of the plug according to FIG. 8, viewed in the direction of the arrow Y of FIG. 8.

The plug-in connector 2 is provided with a correspondingly shaped recess 55 on its lower side that faces the holding plate 4. The T-shaped profile of the interlocking projection 53 may be inserted into this recess. This recess is illustrated in FIG. 9 by a broken line 55. The recess 55 has an opening 56 that extends in the longitudinal direction of the plug-in connector 2, whereby the vertical crosspiece of the interlocking projection 53 engages with the aforementioned opening. The two walls 57 and 58 that are situated opposite one another and are separated from one another by the recess 56 form opposing limit stops 59 and 60 on the end of the cable, where in said opposing limit stops come into contact with the wall 54, and consequently limit the longitudinal displacement of the plug-in connector. FIG. 11 shows that the plug-in connector 2 is pushed onto the projection 52 or the interlocking projection 53 until it reaches the limit stop 54 from the side of the holding plate 4. The plug-in connector is then rigidly connected to the holding plate. Subsequently, the pressure transducer 1 is pushed onto the holding plate and held between two guides 57 and 58. During this movement, the plug-in connector is automatically coupled until the final position illustrated in FIG. 1 has been reached. A spring arm 63 with an interlocking projection 64 is provided in the holding plate 4, wherein this interlocking projection 64 engages behind an edge 65 of the pressure transducer and secures said pressure transducer against unintentional removal. Consequently, the electric plug connection between the plug-in connector 2 and the pressure transducer 1 is fixed in all directions and may not be separated unintentionally. In order to decouple this connection, a push button 61 of the spring arm 63 must be depressed until the interlocking projection 64 releases the edge 65 and the pressure transducer 1 can be pulled out of the holding plates.

As various changes could be made in the above embodiments without departing from the scope of the invention, it is intended that all matter contained in the above description shall be interpreted as illustrative and not in a limiting sense.

What is claimed is:

1. A pressure transducer for measuring the pressure of a fluid, in particular for invasive blood pressure measurements, the pressure transducer comprising:

a housing having a first chamber and a second chamber that are separated from one another in fluid-proof fashion, wherein the first chamber contains a pressure measuring element that may be charged with a fluid having a pressure to be measured and the second chamber contains electronic connection means for connecting an electric cable to an electrical conductor that is connected to the pressure measuring element, and wherein the pressure measuring element is fastened onto a flat substrate, the electric conductor being arranged on the substrate and extending laterally to contact points on the edge of the substrate;

the electronic connection means comprising a plug-in connector;

the second chamber of the housing being accessible from the outer side of the housing via an opening that serves for accommodating the plug-in connector;

the substrate lying centrally in the opening, so that both sides of the substrate lying in the second chamber are accessible via the opening;

the plug-in connector being provided with two parallel tongues between which the substrate may be accommodated, whereby one tongue is provided with electric spring contacts that may be brought in contact with the contact points of the substrate, said electric spring contacts being positioned on the side of said one tongue that faces the other tongue;

the substrate being held by a housing cover that lies parallel to said substrate; and the parallel tongues enclosing the housing cover and the substrate between them.

2. The pressure transducer according to claim 1 wherein the housing cover is fastened onto the housing in detachable fashion.

3. The pressure transducer according to claim 1 wherein the housing cover is provided with a recess for accommodating the tongue of the plug-in connector on its face side that points toward the opening.

4. The pressure transducer according to claim 1 wherein the housing cover has a flat base that adjoins the substrate in assembled condition.

5. The pressure transducer according claim 1 wherein the first chamber is sealed by means of a first annular seal that contacts the substrate and extends around the pressure measuring element.

6. The pressure transducer according to claim 5 wherein an additional annular seal is arranged in the base of the housing cover such that it is situated essentially congruent to the first annular seal, whereby said additional annular seal presses against the side of the substrate situated opposite the first chamber.

7. The pressure transducer according to one of claim 1 wherein the substrate is loosely inserted into the housing and secured against removal by means of a detachable cover for the housing.

8. The pressure transducer according to claim 1 wherein a three-way valve and a rinsing system are integrated into the housing of the pressure transducer.

9. The pressure transducer according to claim 1 wherein the housing is provided with an opening for accommodating and guiding a test key within the region of the second chamber and opposite to the substrate, wherein the side of the test key that faces the substrate carries at least one electronic switching contact that cooperates with switching contact surfaces arranged on the substrate.

10. The pressure transducer according to claim 1 wherein the plug-in connector comprises a recess whereby said plug-in connector may be fixed onto a locking projection of a holding plate, and that the holding plate is provided with guides for guiding and retaining the pressure transducer, wherein said guides and locking projections are mutually aligned in such a way that the plug-in connector and the pressure transducer may be coupled to one another.

11. A pressure transducer for measuring the pressure of a fluid, in particular for invasive blood pressure measurements, the pressure transducer comprising:

a housing having a first chamber and a second chamber that are separated from one another in fluid-proof fashion, wherein the first chamber contains a pressure measuring element that may be charged with a fluid having a pressure to be measured and the second chamber contains electronic connection means for connecting an electric cable to an electrical conductor that is connected to the pressure measuring element, and wherein the pressure measuring element is fastened onto a flat substrate, the electric conductor being arranged on the substrate and extending laterally to contact points on the edge of the substrate;

the electronic connection means comprising a plug-in connector;

the second chamber of the housing being accessible from the outer side of the housing via an opening that serves for accommodating the plug-in connector;

the substrate lying centrally in the opening, so that both sides of the substrate lying in the second chamber are accessible via the opening;

the plug-in connector being provided with first and second parallel tongues between which the substrate may be accommodated, whereby said first tongue is provided with electric spring contacts for contacting the contact points of the substrate, said spring contacts being positioned on the side of the first tongue facing the second tongue;

the substrate being held by a housing cover that lies parallel to said substrate, said housing cover being detachably fastened onto the housing; and the first and second tongues encompassing the housing cover and the substrate between said tongues so that both the housing cover and the substrate are supported by the tongues and mechanical forces generated by the electrical spring contacts on the first tongue are absorbed by said parallel tongue.

* * * * *